United States Patent [19]
Wilks

[11] Patent Number: 6,052,823
[45] Date of Patent: Apr. 25, 2000

[54] COMBINATION SUN PROTECTOR AND SUN GLASSES

[76] Inventor: Charles E. Wilks, 5942 Forest Grove Blvd., Orlando, Fla. 32808

[21] Appl. No.: 09/267,059

[22] Filed: Mar. 12, 1999

[51] Int. Cl.⁷ ...................................................... A61F 9/00
[52] U.S. Cl. ......................... 2/13; 2/12; 2/452; 351/155; D16/310
[58] Field of Search ............................. 2/10, 12, 13, 171, 2/195.1, 209.3, 209.4, 452, DIG. 11; 351/155, 156, 157; D16/310

[56] References Cited

U.S. PATENT DOCUMENTS

| | | |
|---|---|---|
| D. 320,609 | 10/1991 | Cross et al. . |
| D. 385,898 | 11/1997 | Fujimoto . |
| 4,781,451 | 11/1988 | McAllen . |
| 5,007,109 | 4/1991 | Wheeler . |
| 5,105,475 | 4/1992 | Lynd et al. . |
| 5,105,476 | 4/1992 | Cox . |
| 5,309,577 | 5/1994 | Buononato et al. . |
| 5,519,460 | 5/1996 | Mills . |
| 5,687,837 | 11/1997 | Seiler . |
| 5,826,271 | 10/1998 | Garrett . |

*Primary Examiner*—Diana Oleksa
*Attorney, Agent, or Firm*—John V. Stewart

[57] ABSTRACT

Sunglasses and a sun visor attached to a headband in an opposed configuration, such that only one or the other accessory is used at a given time. The alternate accessory is carried behind the head where it serves to close the circle of the headband. This secures the device on the user's head during vigorous activity and in windy conditions such as encountered in beach sports, cycling, boating, skateboarding, etc.. The user wears either the sunglasses or visor forward, thus protecting the eyes with the sunglasses, or allowing full ventilation for the eyes on hot days by using the visor. In addition to its practical uses, the unique appearance of the device provides a marketable attraction.

6 Claims, 5 Drawing Sheets

COMBINATION SUN PROTECTOR AND SUN GLASSES

BACKGROUND OF THE INVENTION

1. Field of the Invention

This invention is in the fields of sunglasses and visors.

2. Description of Prior Art

U.S. Pat. No. 5,826,281 (Garret) shows a sun visor with attached sunglasses which are rotatable incrementally between up, down, and intermediate positions under the visor. The sunglasses are attached below the visor in the same orientation, not diametrically opposed as in the present invention.

U.S. Pat. No. D320,609 (Cross et al) show a sun visor which can be attached to sunglasses by sliding an elastic tube on each side of the visor over the temples of the glasses. This device is not shown in use, but it cannot be used in the diametrically opposed configuration of the present invention. It is shown as a single sheet of material that is simply sewn to create the flexible tubes. The tubes must be elastic to slip over and grip the temples of the frame, thus the visor must also be elastic. The visor is clearly not designed for the tension required to serve both as a head-encircling retention strap and a visor. It would buckle under this stress, becoming useless as a visor. Therefore, it must be assembled above the lenses of the glasses, where the glass frames provide rigidity.

There are other prior patents showing of combinations of sunglasses and visors, but there is no suggestion in them for combining these elements in the diametrically opposed configuration of the present invention.

SUMMARY OF THE INVENTION

An objective of the present invention is means for providing both sunglasses and a sun visor in one assembly worn on the head, such that either type of sun protection is alternately available, and both types are conveniently carried. Another objective is a unique style of headwear that is instantly noticeable, memorable, and recognizable in either of two orientations.

The objectives of the present invention are achieved by the combination of sunglasses and a sun visor attached to a headband in an opposed configuration, such that only one or the other accessory is used at a given time. The alternate accessory is carried behind the head where it serves to close the circle of the headband. This secures the device on the user's head during vigorous activity and in windy conditions such as encountered in beach sports, cycling, boating, skateboarding, etc. The user wears either the sunglasses or visor forward, thus protecting the eyes with the sunglasses, or allowing full ventilation for the eyes on hot days by using the visor. In addition to its practical uses, the unique appearance of the device provides a marketable attraction.

REFERENCE NUMBERS

Figure 1:
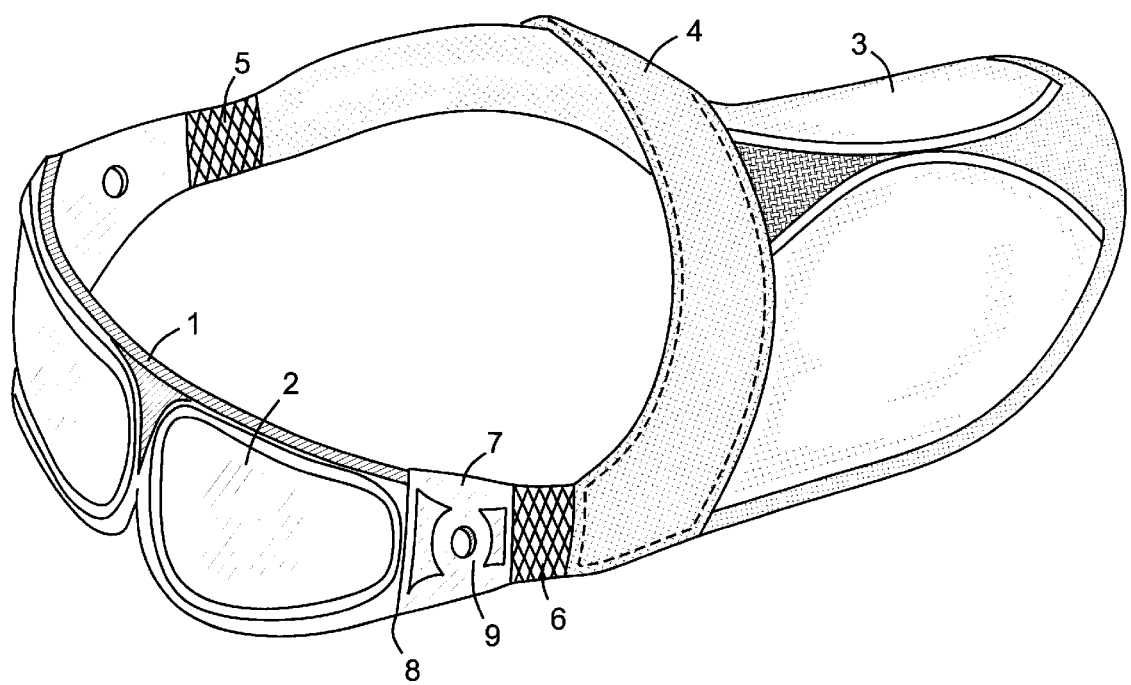
FIG. 1 is a perspective view of the device. The hidden surfaces are preferably mirror images of the visible surfaces in this view, with the exception of the band 4, which is preferably overlapping, as best seen in FIG. 3.
Figure 2:
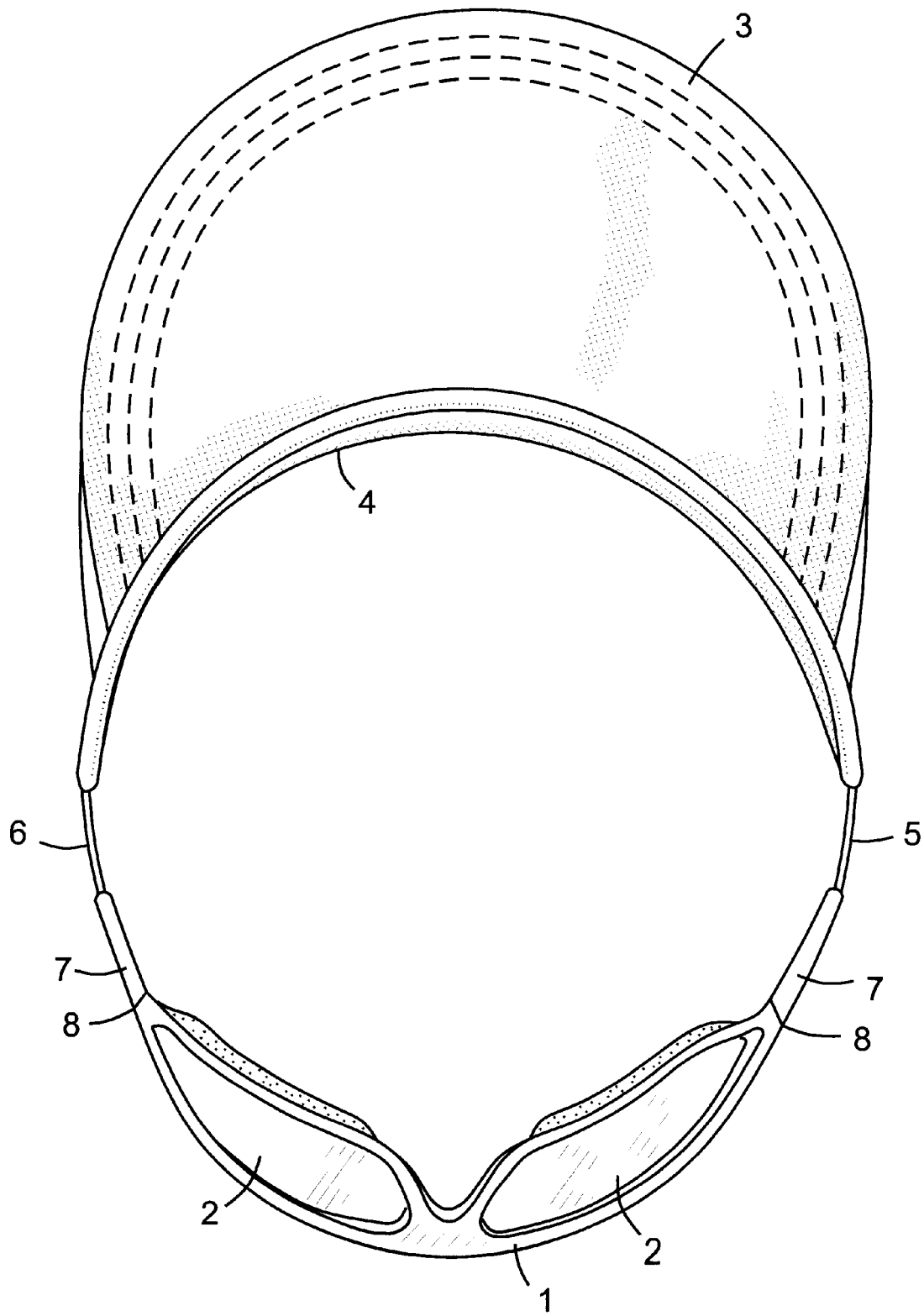
FIG. 2 is a bottom view of the device.

1. Frame of sunglasses
2. Lens of sunglasses
3. Visor
4. Band of visor
5. First Strap
6. Second Strap
7. Temple
8. Hinge
9. Adjustment means
10. Removable sunglass cover
11. First part of hook-and-loop fastener material
12. Second part of hook-and-loop fastener material

Terminology

Left, right

The left and right sides of the device reverse positions depending on the orientation of the device on a user's head. The left side of the visor is to the left side of the user when the visor is on the front of the user's head. The left side of the sunglass frame is to the left side of the user when the sunglasses are on the front of the user's head. Thus, the left side of the visor is attached to the right side of the sunglass frame.

Description of the preferred embodiments

FIG. 1 shows an example of the preferred embodiment of the invention, comprising a pair of sunglasses 1 and a visor 3, which are attached to each other back-to-back with side straps 5 and 6. The side straps are preferably elastic and/or adjustable in length to accommodate different head sizes. The assembly forms a circle to be worn on a user's head with either the sunglasses or visor forward. The part that is not used is carried conveniently behind the head, not requiring a pocket or bag, and not subject to misplacement or loss. The user can thus choose the most appropriate side for use, depending on conditions and preference. In addition, the unique appearance of the device makes the user highly noticeable.

The straps preferably have conventional length adjustment means such as hook-and-loop material, buckles, knobs and a matching series of holes, or the like. The sunglass frames are preferably semi-flexible to conform to the user's face for maximum protection from the sun and wind-blown particles. They can be in a conventional form of ski goggles, motorcycle goggles, beach sunglasses, or the like. Two suggested designs are shown in the drawings. Since the device is secured around the user's head, it is useful for windy conditions as encountered in skiing, cycling, and the like.

Figure 3:
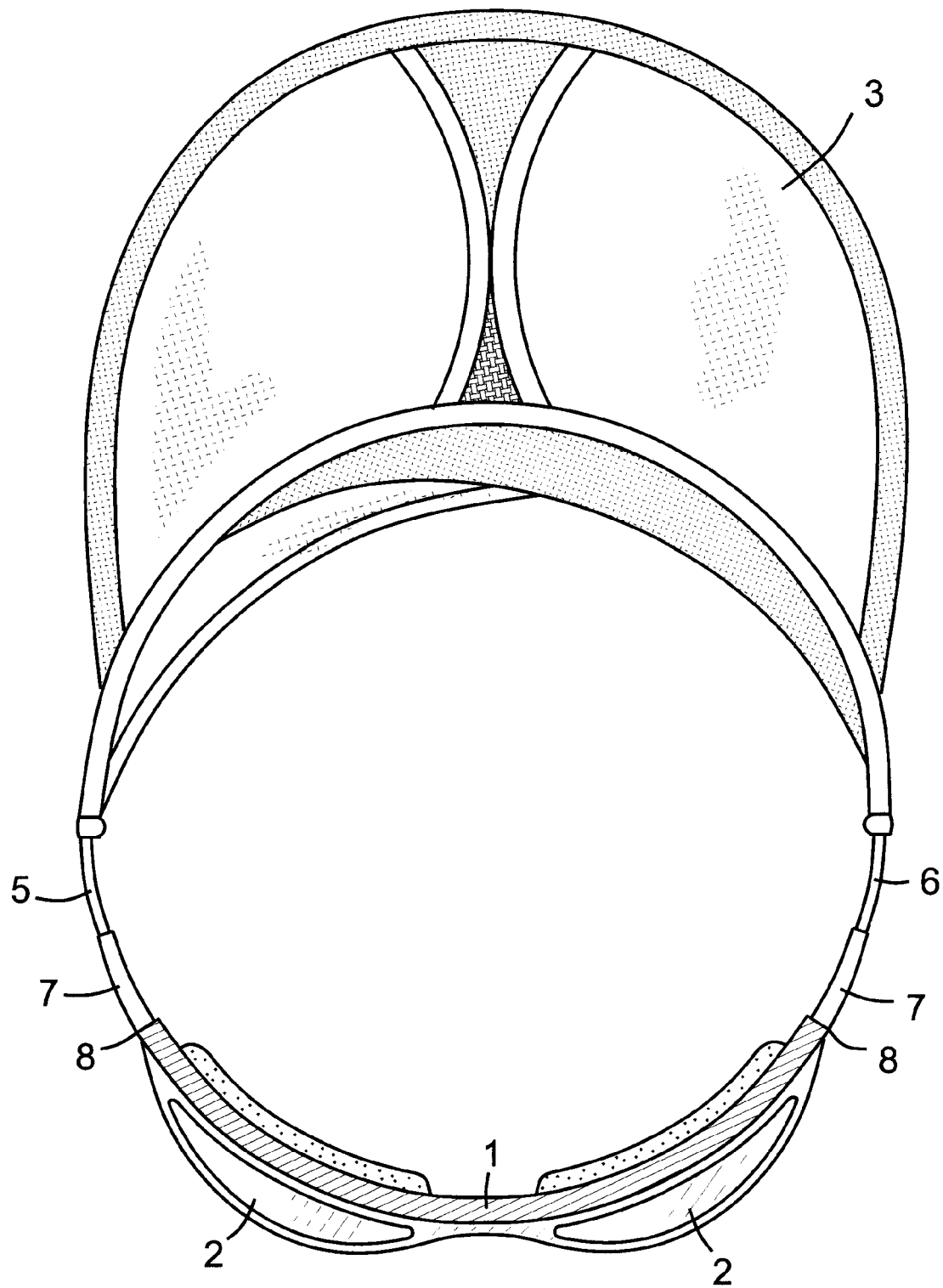
FIG. 3 is a top view of the device.

The visor has a band 4 that distributes pressure on the users head. The band also provides angular stability for the visor, preventing it from collapsing flat against the user's head. Thus, the band should include a semi-rigid portion as with a conventional hat or visor band. It may also have a decorative covering, such as overlapping fabric, as shown in FIG. 3, and a sweat absorbing inner layer. The band can extend backward from the visor and attach directly to the sunglass frame. However, the side straps 5 and 6 are preferably separate parts, allowing for adjustability. The side straps and band can be considered to form a continuous loop between the sides of the sunglass frames for encircling the head, whether adjustable or not.

The temples of the sunglasses can be made of a rigid or semi-rigid material such as plastic, but they preferably do not include ear hooks. They are preferably hinged, and are just long enough to provide attachment for the side straps. They can optionally be in the form of buckles that allow the side straps to be adjusted therein. Such temples can be eliminated by attaching the side straps directly to the sides of the sunglass frames. In this case, the side straps can be adjusted by other means, such as alternate attachment points for the ends of the side straps on the visor band 4.

Figure 6:
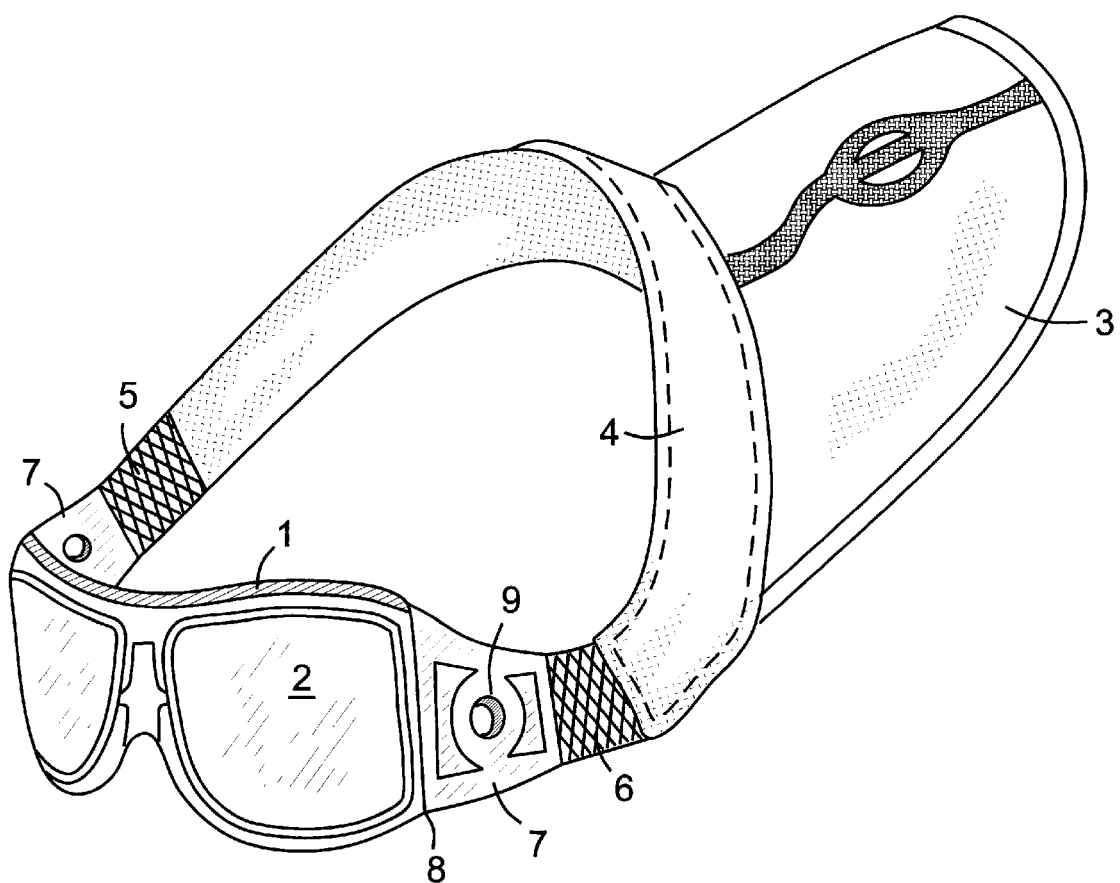
FIG. 6 is a perspective view of the device with alternate decoration.

The visor is preferably decorated with an artistic design, such as the two examples shown in FIGS. 1 and 6.

Figure 4:
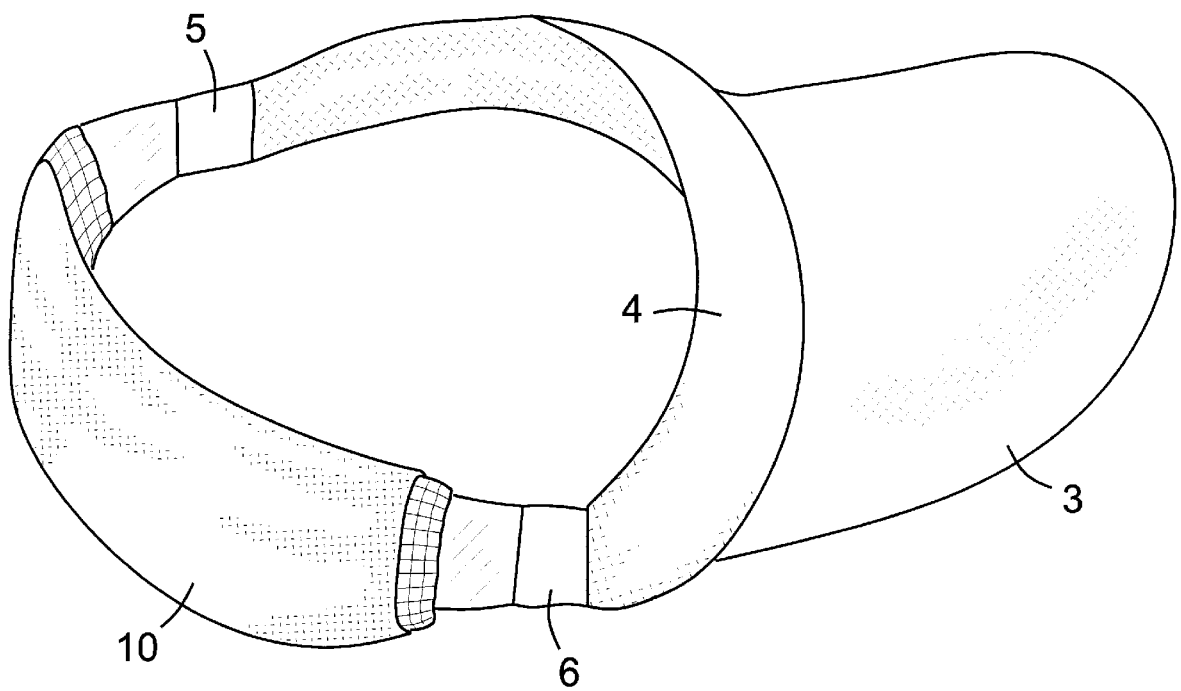
FIG. 4 is a perspective view of the device with an optional removable cover on the sunglasses.
Figure 5:
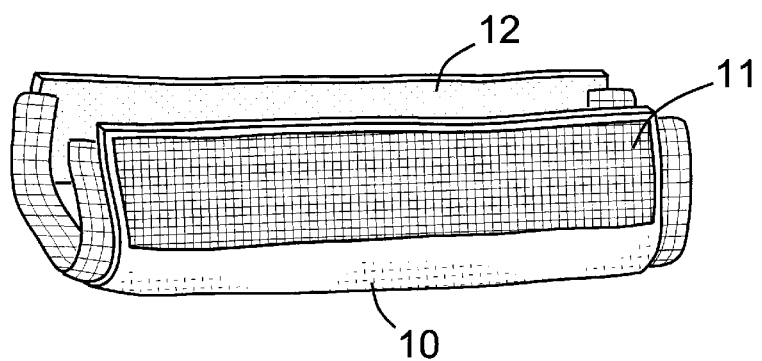
FIG. 5 is a perspective view of the optional removable cover for the sunglasses.

An optional removable protective cover 10 for the sunglasses may be provided as shown in FIGS. 4 and 5. It is preferably made of a flexible material, such as fabric, with hook-and-loop type fastening material 11, 12.

Although the present invention has been described herein with respect to preferred embodiments, it will be understood that the foregoing description is intended to be illustrative, not restrictive. Modifications of the present invention will occur to those skilled in the art. All such modifications that fall within the scope of the appended claims are intended to be within the scope and spirit of the present invention.

I claim:

1. A combination sun protector and sunglasses, comprising;

sunglasses having a front and a back;

a sun visor having a front and a back;

two side straps; and the sunglasses and the visor connected to each other back-to-back with the side straps in a generally circular assembly for encircling a user's head;

whereby a user can wear the assembly on his head with the sunglasses before his eyes and the visor behind his head, or he can reverse the assembly and wear the visor over his eyes and the sunglasses behind his head.

2. The combination sun protector and sunglasses of claim 1, further comprising a sheet of flexible material with hook-and-loop fastening means forming a removable cover for the sunglasses.

3. A combination sun protector and sunglasses, comprising:

a frame holding a pair of sunglass lenses, the frame having left and right sides and a front;

a sun visor having left and right sides and a front;

first and second straps; and the frame and visor connected to each other in opposite-facing directions by means of the first strap connected between the left side of the frame and the right side of the visor, and the second strap connected between the right side of the frame and the left side of the visor;

the combination generally forming band for encircling a user's head;

whereby a user can wear the combination sun protector and sunglasses on his head with the sunglass lenses before his eyes and the visor behind his head, or he can reverse the combination and wear the visor over his eyes and the sunglass frame behind his head.

4. A combination sun protector and sunglasses, comprising:

a sun visor having a front and a back;

a sunglass frame having a front, a back, and first and second sides;

a loop having a central portion and first and second ends, the ends of the loop attached to respective sides of the sunglass frame;

at least the central portion of the loop being a semi-rigid material;

the back of the visor attached to the central portion of the loop, so that the visor and the sunglass frame are facing in opposite directions;

whereby a user can wear the sunglass frames before his eyes, and the visor behind his head, or alternately, the visor over his eyes, and the sunglass frames behind his head.

5. The combination sun protector and sunglasses of claim 4, wherein the ends of the loop are attached to the central portion of the loop by adjustment means for varying the length of the loop.

6. The combination sun protector and sunglasses of claim 4, wherein the ends of the loop comprise temples attached by hinges to the sides of the sunglass frame.

\* \* \* \* \*